United States Patent
Zeiher et al.

(10) Patent No.: US 9,062,307 B2
(45) Date of Patent: Jun. 23, 2015

(54) ANTAGONISTS OF MIRNA-29 EXPRESSION AND THEIR USE IN THE PREVENTION AND TREATMENT OF ANEURYSM

(75) Inventors: Andreas Zeiher, Frankfurt (DE); Stefanie Dimmeler, Frankfurt (DE); Reinier Boon, Frankfurt (DE)

(73) Assignee: Johann Wolfgang Goethe-Universität Frankfurt am Main, Frankfurt am Main (DE)

( * ) Notice: Subject to any disclaimer, the term of this patent is extended or adjusted under 35 U.S.C. 154(b) by 0 days.

(21) Appl. No.: 13/637,924

(22) PCT Filed: Apr. 1, 2011

(86) PCT No.: PCT/EP2011/055122
§ 371 (c)(1),
(2), (4) Date: Jan. 22, 2013

(87) PCT Pub. No.: WO2011/121120
PCT Pub. Date: Oct. 6, 2011

(65) Prior Publication Data
US 2013/0116303 A1      May 9, 2013

(30) Foreign Application Priority Data

Apr. 1, 2010 (EP) .................................... 10003675

(51) Int. Cl.
| | | |
|---|---|---|
| *C12N 15/11* | (2006.01) | |
| *C12Q 1/68* | (2006.01) | |
| *C12N 15/113* | (2010.01) | |
| *A61K 31/7088* | (2006.01) | |
| *C12Q 1/02* | (2006.01) | |

(52) U.S. Cl.
CPC .......... *C12N 15/113* (2013.01); *A61K 31/7088* (2013.01); *C12N 2310/113* (2013.01); *C12Q 1/025* (2013.01)

(58) Field of Classification Search
None
See application file for complete search history.

(56) References Cited

U.S. PATENT DOCUMENTS

2009/0226375 A1* 9/2009 Olson et al. ................... 424/9.2

FOREIGN PATENT DOCUMENTS

| WO | WO 2009/018493 A1 | 2/2009 |
| WO | WO 2009/075391 A1 | 6/2009 |

OTHER PUBLICATIONS

Rooij et al, Dysregulation of microRNAs after myocardial infarction reveals a role of miR-29 in cardiac fibrosis, 2008, PNAS, vol. 105, 35: 13027-13032.*
Daugherty et al, Mechanisms of Abdominal Aortic Aneurysm Formation, 2002, Current Atherosclerosis Reports, 4: 222-227.*
Akagawa et al, A haplotype spanning two genes, ELN and LIMK1, decreases their transcripts and confers susceptibility to intracranial aneurysms, 2006, Human Molecular Genetics, vol. 15, No. 10, 1722-1734.*
Ott et al, Fail-Safe mRNA/microRNA Network Motif is Associated with Down-Regulation of Elastin in Postnatal Aortic Development, Feb. 2010, Medizinische Genetik, vol. 22, 1: 71-72, Abstract # W2-02.*
Boon R.A. et al., "MicroRNA-29 Links Aging with Aortic Aneurysm Formation in Mice", *Clin Res Cardiol*, Apr. 9, 2010, vol. 99, Suppl. 1, p. P1057, abstract only.
Golledge, J. et al., "Peroxisome Proliferator-Activated Receptor Ligands Reduce Aortic Dilatation in a Mouse Model of Aortic Aneurysm", *Atherosclerosis*, 2010, vol. 210, No. 1, pp. 51-56.
Jones, A. et al., "Rosiglitazone Reduces the Development and Rupture of Experimental Aortic Aneurysms", *Circulation*, Jun. 23, 2009, vol. 119, No. 24, pp. 3125-3132.
Yumei, Y. et al., "Down-Regulation of MicroRNA-29 Contributes to the Myocardial Protective Effect of Pioglitazone against Ischemia-Reperfusion Injury—a PPAR-gamma Dependent Effect", *Journal of the American College of Cardiology*, Mar. 2009, vol. 53, No. 10, Suppl. 1, p. A311, abstract only.

* cited by examiner

*Primary Examiner* — Tracy Vivlemore
*Assistant Examiner* — Kate Poliakova
(74) *Attorney, Agent, or Firm* — Saliwanchik, Lloyd & Eisenschenk

(57) ABSTRACT

The present invention relates to antagonists of the expression and/or the function of the micro RNA miRNA-29 for use in the prevention and/or treatment of aortic aneurysms. Further disclosed is a method for the identification of miRNA-29 antagonists, a pharmaceutical composition comprising said miRNA-29 antagonists and a method for preventing and treating age-related aortic aneurysm formation in a subject in need of such a treatment.

9 Claims, 7 Drawing Sheets

A)

A

B

ANTAGONISTS OF MIRNA-29 EXPRESSION AND THEIR USE IN THE PREVENTION AND TREATMENT OF ANEURYSM

CROSS-REFERENCE TO A RELATED APPLICATION

This application is a National Stage Application of International Application Number PCT/EP2011/055122, filed Apr. 1, 2011; which claims priority to European Application No. 10003675.5, Apr. 1, 2010; which are incorporated herein by reference in their entirety.

FIELD OF THE INVENTION

The present invention relates to antagonists of the expression and/or the function of the micro RNA miRNA-29 for use in the prevention and/or treatment of aortic aneurysms. Further disclosed is a method for the identification of miRNA-29 antagonists, a pharmaceutical composition comprising said miRNA-29 antagonists and a method for preventing and treating age-related aortic aneurysm formation in a subject in need of such a treatment.

BACKGROUND OF THE INVENTION

The present-day extension of human lifespan comes at the cost of increased prevalence of aging-associated cardiovascular diseases (Lakatta E C. Age-associated cardiovascular changes in health: impact on cardiovascular disease in older persons. *Heart Fail Rev.* 2002; 7:29-49). One particular condition with high mortality is aortic aneurysm formation and subsequent rupture of the aortic vessel. Aortic aneurysm (AA) is a typical age-associated disease that affects approximately 9% of elderly men and leads to a significant number of death (Singh K, Bonaa K H, Jacobsen B K, Bjork L, Solberg S. Prevalence of and Risk Factors for Abdominal Aortic Aneurysms in a Population-based Study: The Tromso Study. *Am J. Epidemiol.* 2001; 154:236-244).

The incidence of AA is still increasing indicating that current primary preventive health care strategies e.g. by targeting blood pressure are not sufficiently effective in reducing AA. Surgery is currently the state-of-the-art treatment; however, this surgical intervention is associated with a significant morbidity and mortality, e.g. only 10-25% of patients survive rupture due to large pre-and post-operative mortality. On a mechanistic level, analysis of human pathological sections revealed that AA formation and rupture are characterized by thinning of the vascular wall. Decreased formation or destruction of extracellular matrix are believed to be the key pathophysiological processes leading to vascular wall thinning (Guo D C, Papke C L, He R, Milewicz D M. Pathogenesis of thoracic and abdominal aortic aneurysms. Ann N Y Acad Sci. 2006; 1085:339-352).

MicroRNAs (miRNAs) have recently emerged as key regulators of several (patho-) physiological processes miRNAs are short non-coding RNAs that regulate protein expression post-transcriptionally by inducing degradation of the targeted mRNA or by blocking protein translation. miRNAs are expressed as precursor transcripts which fold into a stem-loop structure. Precursor miRNAs are sequentially digested via the Drosha and Dicer nucleases to yield the mature miRNA duplex, which is then introduced into the miRNA associated RNA induced silencing complex (RISC). However, only one strand of the mature miRNA is retained in the complex and will provide the binding to the targeted mRNA. The target-sequence regions within the silenced gene transcript are mostly found in the untranslated regions of the respective mRNA; miRNAs bind preferably in the 3' untranslated region of their target mRNA and facilitate translational inhibition or mRNA degradation.

Whereas various studies showed that specific miRNAs control vessel growth and cardiac function (Urbich C, Kuehbacher A, Dimmeler S. Role of microRNAs in vascular diseases; inflammation, and angiogenesis. *Cardiovasc Res.* 2008; 79:581-588), the involvement of miRNAs in AA formation and atherosclerotic plaque rupture and the impact of age on the expression of vascular miRNAs is unknown.

The microRNA family around miRNA-29 is known as a key regulator of fibrosis in cardiac tissue. WO 2009/018493 shows that members of the miRNA-29 family, miRNA-29a, b and c, are down-regulated in the heart tissue in response to stress, and are up-regulated in heart tissue of mice that are resistant to both stress and fibrosis. Aortic aneurysm formation is, however, not disclosed in WO 2009/018493.

Similarly, WO 2008/042231 discloses the therapeutic implications of miRNA expression in diseases of the heart. The altered miRNA expression in cardiomyocytes was found to elicit broad effects on the transcription of various genes in heart failure. For example, miR-1 regulates calmodulin expression levels. Predicted miR-1 targets include several that could contribute to heart failure pathogenesis; among these are Calm 1 and Calm 2, the primary calmodulin isoforms in the heart. The application suggests using miRNAs specifically expressed in affected heart tissue as therapeutic targets.

WO 2009/018493 discloses the use of miR-29a-c antagonists as profibrotic agents to convert soft plaques in the vasculature into fibrotic tissue to prevent myocardial infarction.

Several other MicroRNAs are key regulators in the onset of heart diseases. Silvestri et al. review that MiR-29 is involved in fibrotic reaction after myocardial infarction while miR-21 may exert a fundamental role in post-angioplasty restenosis. MiR-208 is involved in the shift toward a fetal gene expression pattern in contractile proteins in heart failure. MiR-1 influences susceptibility to cardiac arrhythmias after myocardial infarction (Silvestri P et al., MicroRNAs and ischemic heart disease: towards a better comprehension of pathogenesis, new diagnostic tools and new therapeutic targets. *Recent Pat Cardiovasc Drug Discov.* 2009 June; 4(2):109-18).

The expression of miRNA-29 in myocardial infarction is the starting point of a study about the protective effects of Pioglitazone (a PPAR-gamma agonist) against myocardial ischemia-reperfusion injury miRNA-29a and miRNA-29c were significantly less expressed after Pioglitazone administration to rats. Interestingly, Antagomirs of miRNA-29a and miRNA-29c significantly reduced myocardial infarct size and apoptosis in hearts subjected to IR injury. This was probably due to an increased expression of anti apoptotic factors (Mcl-2) in the heart (Ye Y, et al., Down-regulation of microRNA-29 by antisense inhibitors and a PPAR-{gamma} agonist protects against myocardial ischemia-reperfusion injury, Cardiovasc Res. 2010 Feb. 17). Furthermore, Golledge et al. (in Golledge J, et al. Peroxisome proliferator-activated receptor ligands reduce aortic dilatation in a mouse model of aortic aneurysm. Atherosclerosis. 2010 May; 210 (1):51-6. Epub 2009 Oct. 29.) disclose that osteopontin is associated with human abdominal aortic aneurysms (AAA) and that in vitro studies suggest that this cytokine is down-regulated by peroxisome proliferator-activated receptor (PPAR) ligation. Similarly, Jones et al. (in Jones A, et al. Rosiglitazone reduces the development and rupture of experimental aortic aneurysms. Circulation. 2009 Jun. 23; 119(24): 3125-32. Epub 2009 Jun. 8.) discloses that rosiglitazone, a peroxisome proliferator-activated receptor-gamma agonist, reduces aneurysm expansion or rupture. Pretreatment or post-treatment with rosiglitazone reduced aortic expansion and rupture in a mouse model. Reduction of lesions in animals pretreated with rosiglitazone is concomitant with decreased expression of inflammatory mediators. Further studies are described to be needed to elucidate the precise mechanism. Nevertheless, in these publications the effect of the ligands or rosiglitazone or pioglitazone are completely independent from the mechanisms involved in the present invention.

While no drug treatment at all has been approved and is available for a treatment of aortic aneurysm formation, risk factor modifications, as well as preventive therapy using statins and ACE-inhibitors have reduced the mortality due to atherosclerosis during the last 15 years. Most importantly, however, due to the increase in life expectancy and the increased age of the overall population, age-associated diseases like aneurysm formation are expected to further increase over time. Therefore, an efficient treatment is desperately needed. Current attempts to therapeutically interfere with abnormal vessel remodeling exclusively focus on taming the inflammatory response associated with alterations of vascular wall structures. However, there are no therapeutic options at all to modify the structural weakness of the vessel wall. Specific interventions blocking collagen-degrading proteinases or antibody-directed inhibition of recruitment of inflammatory cells turned out to be unsuccessful.

SUMMARY OF THE INVENTION

In view of the prior art described above, and the limitations of preventive or curative strategies currently available for aortic aneurysms, the object of the present invention was to provide novel diagnostic and therapeutic strategies for the prevention and/or treatment of aortic aneurysm formation often diagnosed in elderly people.

In a first aspect the above problem is solved by an antagonist of miRNA-29 expression and/or function for use in the prevention and/or treatment of aortic aneurysm formation in a mammal, preferably a human. By using a bioinformatic approach, the inventors surprisingly found the mir-29 family (mir-29 a, b, and c) to be the only one of the 20 regulated miRNAs as studied in the context of the present invention to functionally affect mRNA levels in the aorta of aged mice, compared to young mice.

Aortic aneurysm formation is caused by breakdown of collagen, fibrillin, apoptosis of vascular smooth muscle cells, and recruitment of inflammatory cells.

The antagonists of the herein described invention are particularly useful for the prevention of diseases and events involving weakening of arterial vessels such as acute myocardial infarction, unstable angina, peripheral arterial occlusive disease, ischemic stroke, aortic aneurysm formation, and aortic rupture. Preferably, the antagonists of the present invention are used for the prevention and/or treatment of conditions, comprising i) aneurysm formation in the aorta due to atherosclerosis, ii) aneurysm formation in the aorta due to genetic causes, for example in the Marfan-Syndrome, iii) aneurysm formation in patients with bicuspid aortic valve formation, and iv) age-dependent aortic aneurysm formation. Thus, in one embodiment, said aortic aneurysm formation can occur in elderly mammals, and thus be age-related. In another embodiment said aortic aneurysm formation can occur because of a genetic condition, and/or is disease-related. Both embodiments can also occur simultaneously.

The term "aortic rupture" in the context of the present invention relates to a condition in which the aorta, the largest artery in the body, is torn or ruptured as the result of dilatation, in particular in consequence of formation of an aortic aneurysm, or as a result of the formation of an atherosclerotic plaque.

The term "prevention" in the context of the present invention shall be understood as a medical intervention which aims to avoid the occurrence of a negative event which most likely leads to the worsening of the condition of a patient having a disease, or to the injury or the death of a healthy and/or ill subject.

In one embodiment the antagonist of miRNA-29 expression and/or function is for use in aortic aneurysm (AA), characterized by the localized dilatation of the aorta due to thinning of the vascular wall.

Therefore, in another embodiment, the antagonist according to the invention are for use in the prevention and/or treatment of age-related aortic aneurysm, wherein said—preferably age-related—aortic aneurysm further involves a down-regulation of the genes for extracellular matrix proteins, such as, for example, for collagens, fibrillin or elastin, in the aortic tissue, such as COL1 A1 COL1 A2, COL1 A3, ELN and/or FBN1.

Yet, in a further embodiment of the invention an antagonist for the expression and/or function of miRNA-29 is selected from an antagonist of the expression and/or function of miRNA-29a, miRNA-29b and miRNA-29c, in particular an antagonist of the expression and/or function of miRNA-29b.

Antagonists according to the present invention are in a further embodiment antagonists selected from antisense DNA- and/or RNA-oligonucleotides, antisense 2'-O-methyl oligoribonucleotides, antisense oligonucleotides containing phosphorothiaote linkages, antisense oligonucleotides containing Locked Nucleic Acid LNA® bases, morpholino antisense oligos, PPAR-gamma agonists, antagomirs, and mixtures thereof.

Since miRNAs target their mRNA by Watson-Crick base-pairing it is preferred that the Antagonist of miRNA-29 is an antisense oligonucleotide, which is complementary to the miRNA and basepairs with the miRNA in competition with the endogenous mRNA target. For the purpose of the invention the sequence of the antisense oligonucleotide is 50% identical to the complement of miRNA-29 (a-c) and/or its seed sequence, preferably 60%, 70%, 80%, 90%, or 95% and most preferably 100% identical to the complement of the miRNA-29 (a-c) and/or its seed sequence. Moreover, particularly preferred are antisense oligonucleotides which are chemically modified to improve the thermal stability of the duplex between the antisense oligonucleotide and the miRNA. Preferred chemical modifications comprise, for example, bicyclic high-affinity RNA analogues in which the furanose ring in the sugar-phosphate backbone is chemically locked in an RNA mimicking N-type conformation by the introduction of 2'-O,4'-C-methylene bridge (LNA®-anti-miRs). Other preferred chemical modified oligonucleotides include morpholinos, 2'-O-methyl, 2'-O-methoxyethyl oligonucleotides and cholesterol-conjugated 2'-O-methyl modified oligonucleotides (antagomirs).

Antagonists in context of the invention also comprise any substance that is able to inhibit miRNA-29 either by inhibiting the expression or by inhibiting the silencing function of the microRNA. Thus, any compound interfering with the microRNA pathway, for example by inhibiting the function of the proteins Pasha, Drosha, Dicer or Argonaut family proteins can be an antagonist according to the invention. Furthermore any compound inhibiting the expression of the precursor microRNA of miRNA-29, such as, for example inhibitors of polymerase II or III are candidate antagonists of miRNA-29 expression. The mature miRNA also serves as a target for the design of inhibitors of miRNA-29 function. Nucleic acids having perfect or mismatched complimentarity to the microRNA may be used to inhibit, or to compete with the binding of the endogenous miRNA-29 with its target mRNA. How to design such miRNA inhibitors is well known in the art.

In a further embodiment the inventive antagonists are administered to the arterial tissue by a drug-eluting stent or by a balloon. Preferably the drug eluting stent or balloon is manufactured of a bioabsorbable material. It is understood that any device suitable for the local delivery of drugs into the interior of a blood vessel may be used in the context of the present invention.

The object of the present invention is solved in another aspect by a method for identifying an antagonist of miRNA-29a to c comprising:
(a) contacting a cell with a candidate compound;
(b) assessing miRNA-29a to c activity or expression; and
(c) comparing the activity or expression in step (b) with the activity or expression of miRNA-29a to c in the absence of the candidate compound,
wherein a decrease between the measured activities or expression of miRNA-29a to c in step (b) compared to step (c) indicates that the candidate compound is an antagonist of miRNA-29a to c.

Suitable cells can be selected from vascular wall cells, cells of aortic origin or other cells derived from mammalian blood vessels, such as, for example, preferably endothelial cells (ECs) and/or smooth muscle cells (SMCs), which in a further preferred embodiment recombinantly or inherently express or preferably overexpress matrix genes, such as, for example, the genes for collagens, fibrillin or elastin, such as COL1A1 COL1A2, COL1A3, ELN and/or FBN1.

In an additional embodiment, the inventive method comprises that the cell is contacted with the candidate compound in vitro and/or in vivo.

Yet another embodiment then relates to an inventive method, wherein the candidate compound is a protein, a peptide, a polypeptide, a polynucleotide, an oligonucleotide or a small molecule.

In a further embodiment, assessing the expression of miRNA-29a to c comprises Northern blotting or RT-PCR. However, there are multiple techniques for the identification and quantification of microRNAs known in the state of the art. In addition to Northern blotting and RT-PCR, assessing microRNA expression can be performed by means of microRNA expression arrays, fluorescent nucleic acid probes, for example coupled to membranes or beads, and antibody based detection systems. In an indirect approach, the activity of the microRNA is further measured by in vitro or in vivo reporter assays. For example, the person of skill in the art could without harnessing inventive skill design reporter assays based on the seed sequence of the miRNA-29 family that allow for an easy screening of candidate miRNA-29 Antagonists. In such an approach the target-sequence of the miRNA could be introduced into the 3' or 5' untranslated regions of a reporter gene of choice. This miR-sensitive construct is then transformed into a suitable cell expression system, which is subsequently brought into contact with the candidate compound. The activity of the reporter gene in samples that were contacted with the compound in comparison with the activity of the reporter gene in control samples gives information about the inhibitory effect of the tested compound.

In yet another embodiment, the inventive method for identifying an antagonist of miRNA-29a to c comprises assessing expression or activity of a gene regulated by miRNA-29a to c, such as, for example, the genes for collagens, fibrillin or elastin, such as COL1A1 COL1A2, COL1A3, ELN and/or FBN1.

In another aspect of the present invention the above problem is solved by a pharmaceutical composition comprising an antagonist of miRNA-29, in particular miRNA-29a to c. In a preferred embodiment the inventive pharmaceutical composition comprises an antagonist of miRNA-29 selected from antisense DNA- and/or RNA-oligonucleotides, antisense 2'-O-methyl oligoribonucleotides, antisense oligonucleotides containing phosphorothiaote linkages, antisense oligonucleotides containing Locked Nucleic Acid LNA® bases, morpholino antisense oligos, PPAR-gamma agonists, antagomirs, and mixtures thereof, and in particular an antagomir of miRNA-29a to c. In a particular preferred embodiment the antagonist of miRNA-29 a to c comprises a sequence that is complementary to the mature sequence of miRNA-29a, miRNA-29b, miRNA-29c, or combinations thereof.

While it is possible that, for use in therapy, an antagonist of miRNA-29a-c expression and/or function may be administered as the raw chemical, it is preferable to present the active ingredient as a pharmaceutical composition. Therefore, in a further aspect, the invention provides a pharmaceutical composition comprising an antagonist of miRNA-29a-c expression and/or function or a pharmaceutically acceptable derivative thereof in association with a pharmaceutically acceptable carrier and/or excipient. The carrier and/or excipient must be "acceptable" in the sense of being compatible with the other ingredients of the formulation and not deleterious to the recipient thereof.

In yet another aspect, the object of the invention is solved by a method of preventing and/or treating aortic aneurysm formation in a subject in need thereof, comprising the steps of:
(a) identifying a subject having an aortic aneurysm formation; and
(b) administering to said subject an antagonist of miRNA-29 expression or function.

A subject in need of prevention and/or treatment of aortic aneurysm formation is in context of the present invention preferably a mammal, more preferably a human, which is diagnosed to have an aneurysm in the aorta. Further comprised is a subject, preferably a mammal, more preferably a human, having an increased risk of developing an aortic aneurysm.

In one embodiment a method as disclosed herein above is preferred, wherein the antagonist of miRNA-29 is selected from antisense DNA- and/or RNA-oligonucleotides, antisense 2'-O-methyl oligoribonucleotides, antisense oligonucleotides containing phosphorothiaote linkages, antisense oligonucleotides containing Locked Nucleic Acid LNA® bases, morpholino antisense oligos, PPAR-gamma agonists, antagomirs, and mixtures thereof, and in particular an antagomir of miRNA-29a to c. In a particular preferred embodiment the antagonist of miRNA-29 a to c comprises a sequence that is complementary to the mature sequence of miRNA-29a, miRNA-29b, miRNA-29c, or combinations thereof.

In a next embodiment a method of preventing and/or treating aortic aneurysm formation in a subject in need thereof is preferred, wherein the antagonist of miRNA-29 is administered by parenteral administration or direct injection into arterial tissue. Such administration of antagonists comprises preferably oral, transdermal, sustained release, controlled release, delayed release, suppository, catheter, drug-eluting stent, balloon, or sublingual administration.

In a further embodiment the method of preventing and/or treating aortic aneurysm formation according to the invention, comprises administering to said subject a second therapy. Preferably said second therapy is selected from the group consisting of the introduction of a stent or a balloon. Most preferred is that said second therapy is administered at the same time as the antagonist of miRNA-29, or wherein said second therapy is administered either before or after the antagonist of miRNA-29.

Preferred is a further embodiment of the method of preventing and/or treating age-related aortic aneurysm formation according to the invention, wherein one or more symptoms of thinning of the vascular wall, and/or a decreased formation or destruction of extracellular matrix proteins is improved in the subject following administration of the antagonist of miRNA-29.

The following figures and examples merely serve to illustrate the invention and should not be construed to restrict the scope of the invention to the particular embodiments of the invention described in the examples. For the purposes of the present invention, all references as cited are hereby incorporated herein by reference in their entireties.

The Examples of the invention refer to the Figures, in which:

FIG. 1 shows a bioinformatic analysis of miRNA and mRNA expression to identify miRNAs that target mRNA Expression. (A) Sylamer landscape using words of a length of 6 nucleotides. The "words" with the highest peaks reflect the miRNA-29 seed sequence. (B) Histogram of miRNA scores. The scores were as follows:

| Mir | score | p-value |
|---|---|---|
| mmu-miR-29c | 26.84 | 2.2e−12 |
| mmu-miR-29b | 26.11 | 4.5e−12 |
| mmu-miR-29a | 23.95 | 3.9e−11 |
| mmu-miR-186 | 13.42 | 1.4e−06 |
| mmu-miR-758 | 10.75 | 2.1e−05 |
| mmu-miR-183 | 10.1 | 4.0e−05 |
| mmu-miR-182 | 9.84 | 5.3e−05 |
| mmu-miR-140 | 9.55 | 7.0e−05 |
| mmu-miR-190 | 9.45 | 7.8e−05 |
| mmu-miR-98 | 8.13 | 0.00029 |

Figure 5:
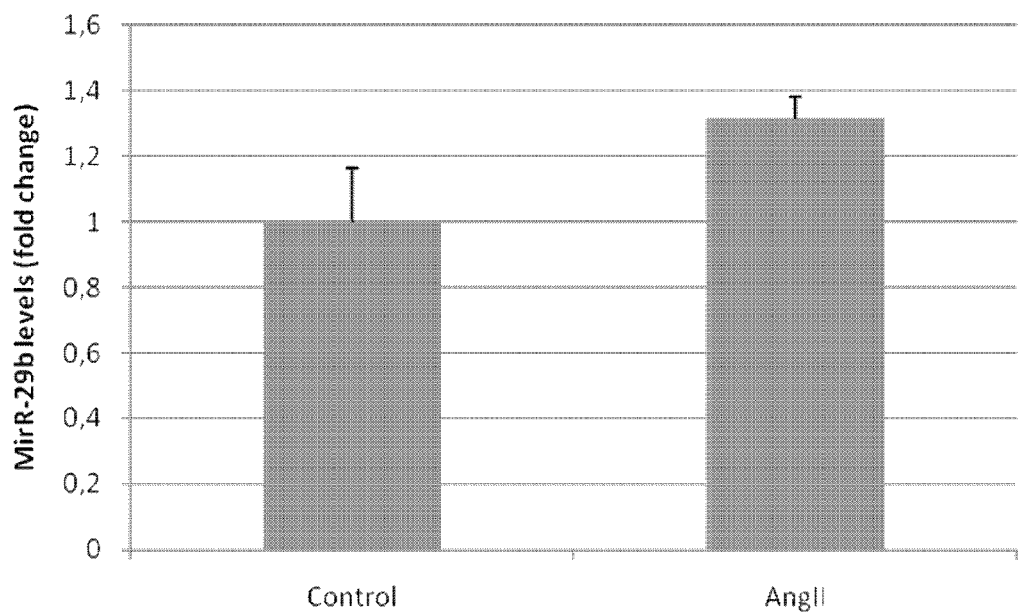
Figure 5:
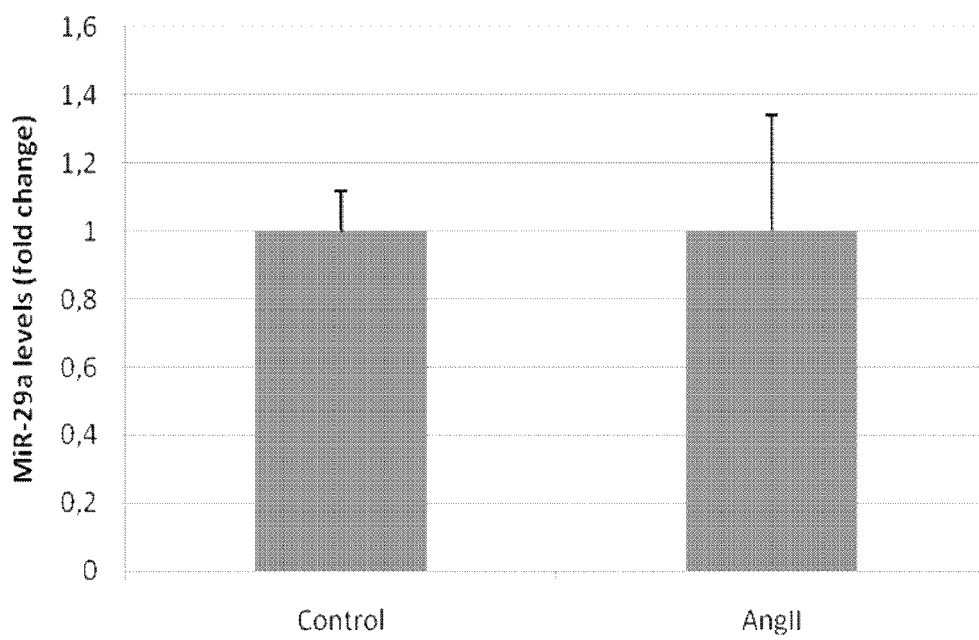
Figure 6:
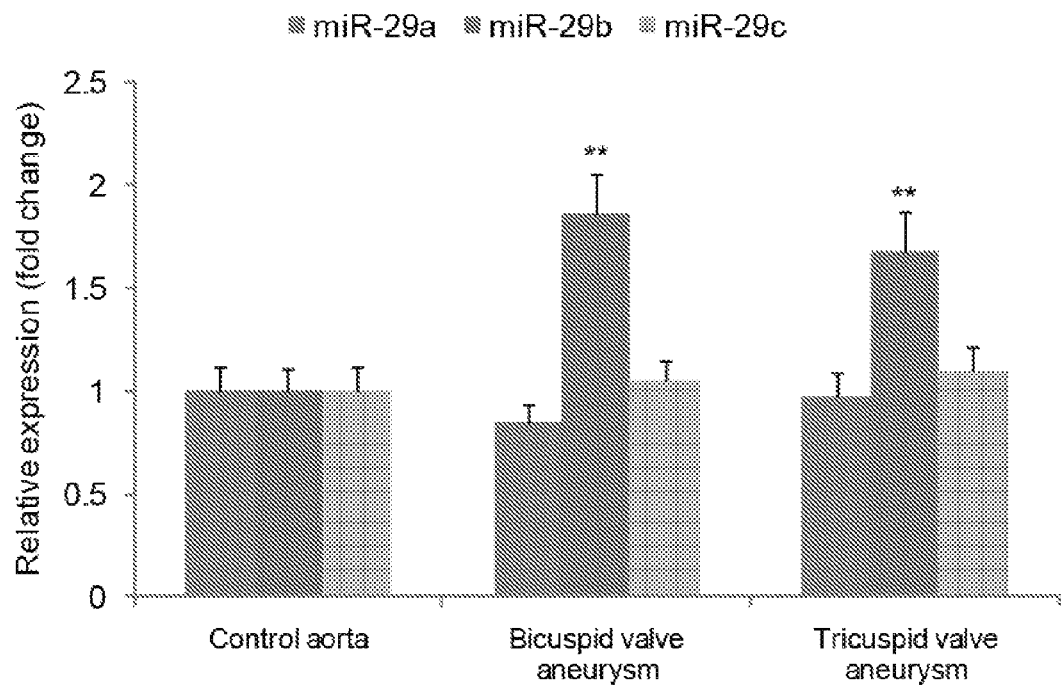

FIG. 5 shows relative MiR-29 (fold change) expression in Ang II treated SMC. (A) miRNA-29b, (b) miRNA-29a FIG. 6 shows the relative expression in fold change of miRNA-29a, miRNA-29b and miRNA-29c in tissue sections of human aortic aneurysms, either of patients with normal tricuspid aortic valves or of patients with abnormal bicuspid aortic valves, compared to a control aorta. (**) indicates a significant difference of expression.

EXAMPLE 1

Age-Related Regulation of miRNAs in the Aorta

In order to determine the effect of age on miRNA expression, the inventors generated miRNA and mRNA micro-array expression profiles comparing aged male mice (18 months old) with young male mice (6 weeks old). 20 miRNAs that are regulated by age [fold increase/decrease>1.5 and p<0.01) in the aorta were identified by this approach (Table 1).

Figure 1:
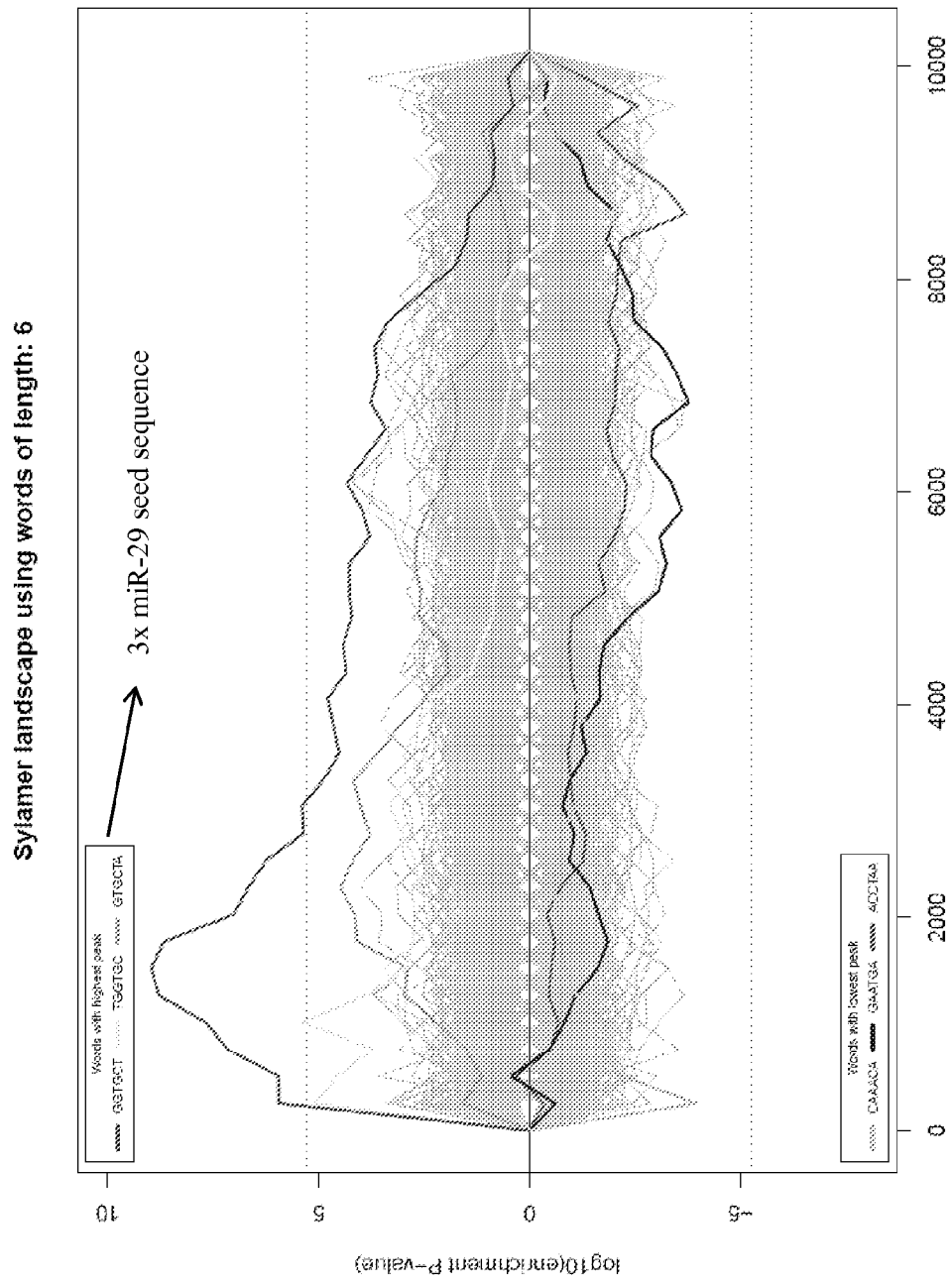
Figure 1:
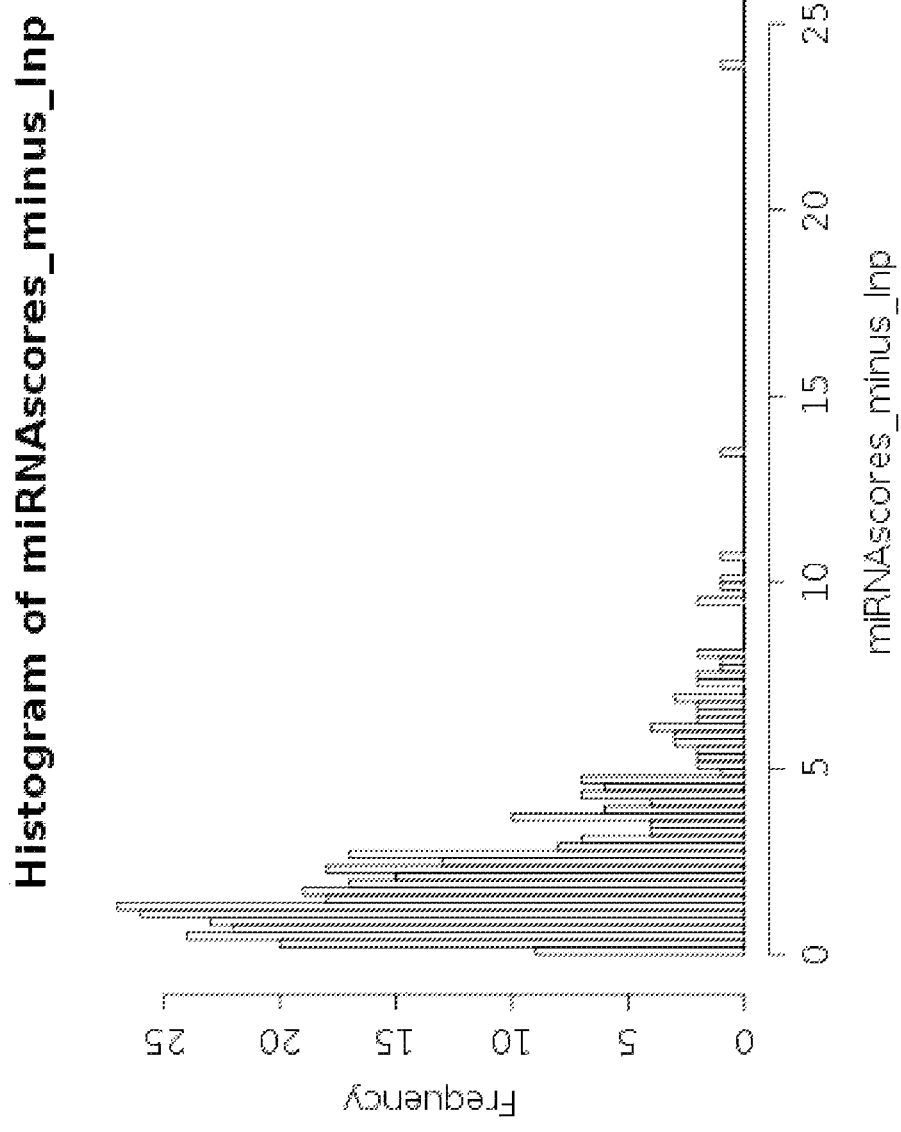
Figure 2:
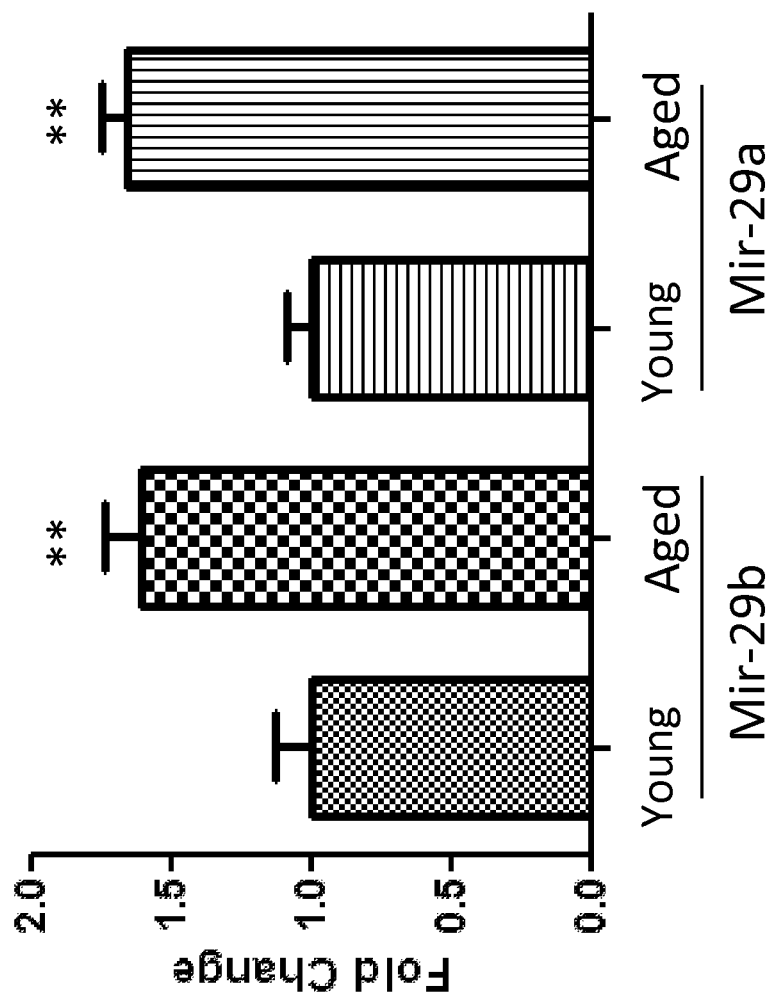
FIG. 2 shows a confirmation of age-regulated miRNAs in the aorta. miRNAs were detected by TaqMan RT-PCR in n=4 young (6 weeks) and n=4 old (18 month) mice. (**) indicates a significant difference between young and aged mice.
Figure 3:
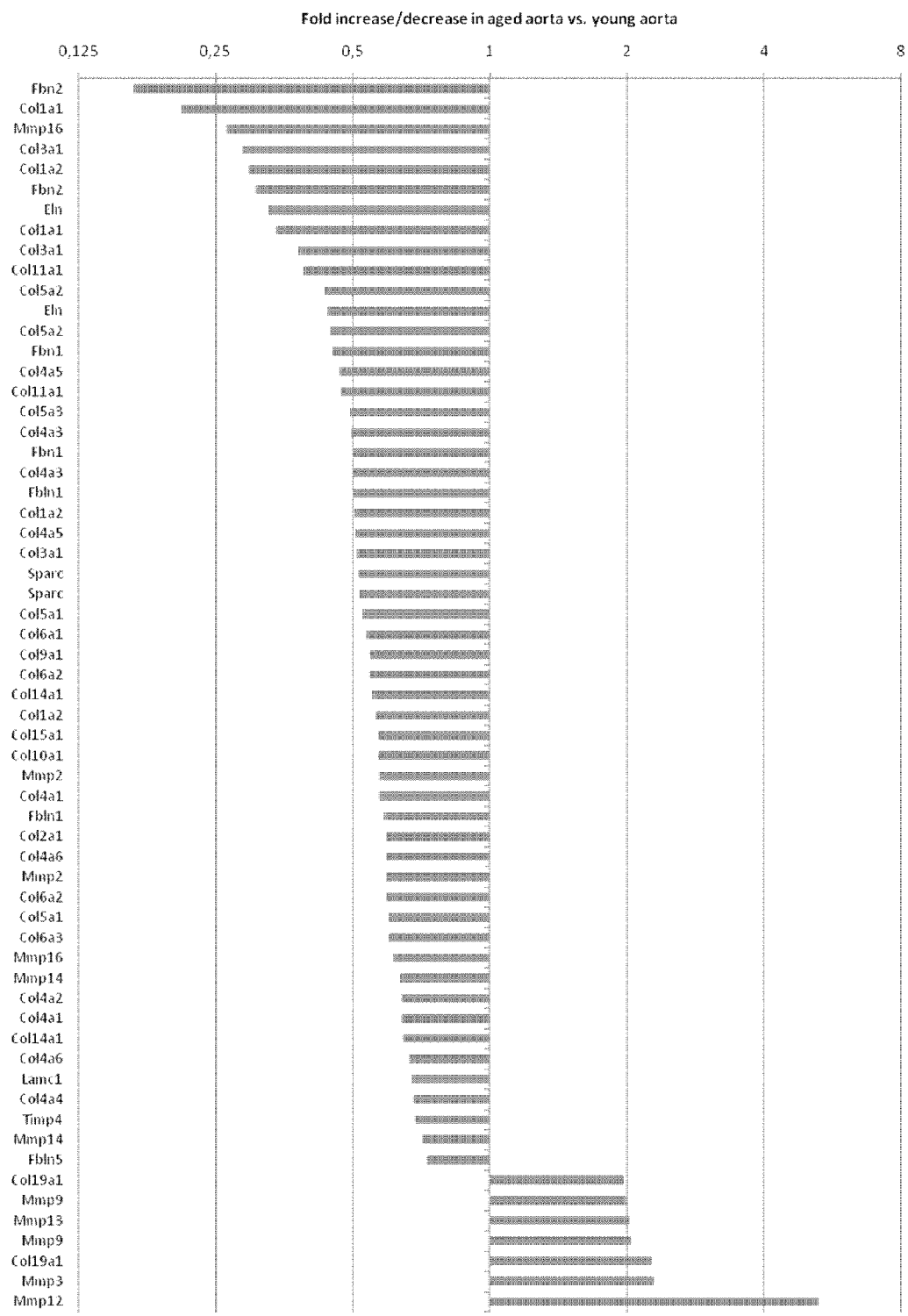
FIG. 3 shows the expression of miRNA-29 target genes in fold increase or fold decrease in aged versus young aorta.

To establish which of these miRNAs also exerts a biological effect in aging, two distinct unbiased bioinformatics tools were applied that use mRNA expression data to identify putative regulation by miRNAs. These tools, Sylamer (van Dongen S et al., Detecting microRNA binding and siRNA off-target effects from expression data. *Nat Meth.* 2008; 5:1023-1025) and MirExTra (http://diana.cslab.ece.ntua.gr/hexamers), both identified the mir-29 family (mir-29a, b and c) to be the only one of the 20 regulated miRNAs to functionally affect mRNA levels (FIG. 1). The up-regulation of the mir-29 family (miRNA-29a and miRNA-29b) by age was confirmed by real-time PCR (FIG. 2). In the heart, the miRNA-29 family (that comprises miRNA-29a, miRNA-29b and miRNA-29c) has been shown to control tissue fibrosis after acute myocardial infarction by targeting extracellular matrix proteins such as collagens, fibrillin and elastin (van Rooij E et al., Dysregulation of microRNAs after myocardial infarction reveals a role of miRNA-29 in cardiac fibrosis. *PNAS.* 2008; 105:13027-13032). Indeed, all of these known targets of mir-29 were down-regulated by age in the aorta (FIG. 3).

TABLE 1

Up-regulated and Down-regulated miRNAs

Up-regulated miRNAs

| Gene Name | fold | FDR-p |
|---|---|---|
| mmu-miR-129-3p | 5.45 | 0.00002 |
| mmu-miR-129-5p | 5.37 | 0.00004 |
| mmu-miR-146a | 2.02 | 0.00671 |
| mmu-miR-142-3p | 1.63 | 0.00599 |
| mmu-miR-29b | 1.61 | 0.00381 |
| mmu-miR-223 | 1.58 | 0.00649 |

Down-regulated miRNAs

| Gene Name | Fold | FDR-p |
|---|---|---|
| mmu-miR-299* | −2.21 | 0.00032 |
| mmu-miR-181c | −2.14 | 0.00028 |
| mmu-miR-127 | −2.10 | 0.00013 |
| mmu-miR-154 | −1.95 | 0.00145 |
| mmu-miR-337-5p | −1.86 | 0.00163 |
| mmu-miR-379 | −1.76 | 0.00150 |
| mmu-miR-136 | −1.71 | 0.00244 |
| mmu-miR-329 | −1.70 | 0.00017 |
| mmu-miR-31 | −1.67 | 0.00246 |
| mmu-miR-322 | −1.67 | 0.00675 |
| mmu-miR-377 | −1.63 | 0.00359 |
| mmu-miR-434-3p | −1.61 | 0.00325 |
| mmu-miR-411 | −1.54 | 0.00052 |
| mmu-miR-181d | −1.51 | 0.00237 |

EXAMPLE 2

Angiotensin II Induces miRNA-29 Expression In Vitro and In Vivo

Figure 4:
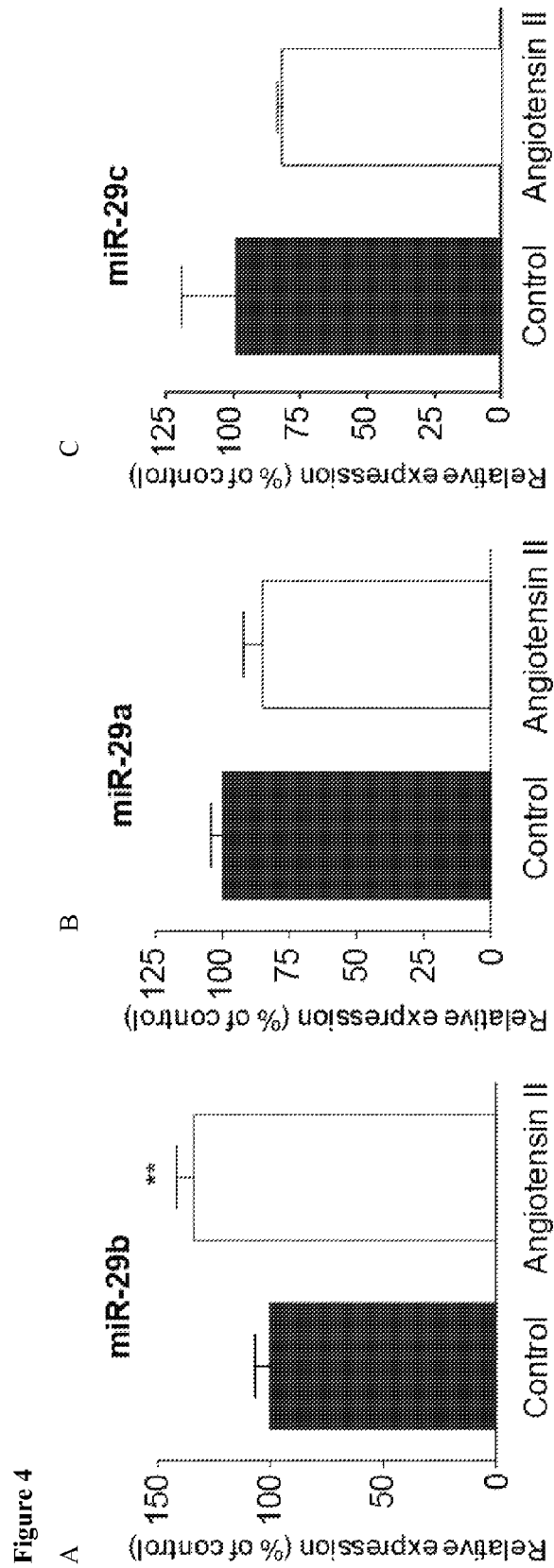
FIG. 4 shows the expression of miRNA-29 family members in the aorta of Ang II-infused mice normalized against sno202. (a) miRNA-29b, (b) miRNA-29a, (c) miRNA-29c. n=6 per group. (**) indicates a significant difference between control and angiotensin treated samples.

Angiotensin (Ang) II infusion in ApoE$^{-/-}$ mice is used as an established model for AA formation in mice. Therefore, Ang II was continuously applied in mice for 4 weeks. In the aorta of Ang II treated mice, miRNA-29b was significantly up-regulated (FIG. 4a). However, the other member of the miRNA-29 family, miRNA-29a, was not regulated (FIG. 4b). These in vivo data were confirmed by in vitro studies showing that Ang II-treatment of smooth muscle cells stimulated miRNA-29b expression but did not affect miRNA-29a (FIG. 5). These data demonstrate that Ang II as a prototypical inducer of AA formation in mice induces miRNA-29b expression.

EXAMPLE 3 miRNA-29b is Specifically Increased in Human Pathological Sections of Aneurysms

To test the relevance of these experimental findings in humans, the expression of miRNA-29 family members in pathological sections of patients with bicuspid aortic valve disease was measured. In this experimental setting, miR-29b, but not miRNA-29a and miRNA-29c was significantly increased in sections of n=77 patients compared to n=30 control aortas (FIG. 6). Nevertheless, without wanting to be bound by theory, it is assumed that in older subjects/patients the regulation of miRNA-29a and miRNA-29c is also modified, as was found in the respective mouse models.

The data of the present study show that age is associated with increased expression of the miRNA-29 family in the aorta. Consistent with the increased expression of miRNA-29 family members, the levels of extracellular matrix proteins that are targeted by miRNA-29 are significantly reduced. Since age comprises a major risk factor for the development of AA, the inventors subsequently determined the regulation of miRNA-29 in aortas of Ang II-infused mice. Ang II is one of the factors that increase the incidence of AA in mice. Like with aging, Ang II infusion augments the expression of miRNA-29b. However, in contrast with aging other members of the miRNA-29 family were not regulated by Ang II infusion. Similarly, Ang II treatment of SMC in vitro also preferentially increased miRNA-29b expression. To determine the putative relevance in humans, the inventors additionally measured the expression of miRNA-29 family members in human pathological sections. Consistent with the experimental findings using Ang II as stimulus, miRNA-29b was selectively and significantly up-regulated in diseased versus control sections of the human aorta. Together these data demonstrate that miRNA-29b is increased by age and by factors stimulating AA in experimental models as well as in humans. Since miRNA-29b targets extracellular matrix proteins, one may speculate that the increased expression of miRNA-29b may contribute to the destruction of extracellular matrix and thinning of the vessel wall.

MiR-29 was additionally shown to induce apoptosis in cancer cells by targeting Mcl-1, an anti-apoptotic Bcl-2 family member (Mott J L et al., mir-29 regulates Mcl-1 protein expression and apoptosis. Oncogene. 2007; 26:6133-6140), and by augmenting p53 levels (Park S Y et al., miRNA-29 miRNAs activate p53 by targeting p85 [alpha] and CDC42. Nat Struct Mol Biol. 2009; 16:23-29). Smooth muscle cell apoptosis is considered to contribute to plaque rupture and may be involved in AA as well (Clarke M C H et al., Chronic Apoptosis of Vascular Smooth Muscle Cells Accelerates Atherosclerosis and Promotes Calcification and Medial Degeneration, Circ Res. 2008; 102:1529-1538). Although it remains to be demonstrated that these pro-apoptotic effects of miRNA-29 also occur in smooth muscle cells, an induction of smooth muscle cell apoptosis by miRNA-29 may further lead to plaque destabilization. Thus, miRNA-29b may be a very attractive target to prevent the thinning and destabilization of atherosclerotic plaques.

Because surgery is the only treatment currently available for AA, a novel pharmacological intervention will provide a major step in the therapy of AA miRNA inhibitors—so called antagomirs or antimiRs—have been successfully used to reduce miRNA expression in mouse models and non-human primates (Bonauer A et al., MicroRNA-92a Controls Angiogenesis and Functional Recovery of ischemic Tissues in Mice. Science. 2009; 324:1710-1713; Lanford R E et al., Therapeutic Silencing of MicroRNA-122 in Primates with Chronic Hepatitis C Virus Infection. Science. 2010; 327:198-201). Local delivery of antagomirs by drug-eluting stents or via balloons may be useful to provide an efficient local suppression of the miRNA in the target tissue and limit putative side effects on other organs.

The invention claimed is:

1. A method for the prevention and/or treatment of aortic aneurysm formation in a mammal, wherein said method comprises administering, to a mammal in need of such prevention and/or treatment, an antagonist of miRNA-29 expression and/or function.

2. The method according to claim 1, wherein said aortic aneurysm is an abdominal aortic aneurysm (AAA) or an age related aortic aneruism.

3. The method according to claim 1, wherein said aortic aneurysm formation further involves aortic rupture.

4. The method according to claim 1, wherein said aortic aneurysm further involves a down-regulation of extracellular matrix protein.

5. The method according to claim 1, wherein said miRNA-29 is selected from miRNA-29a, miRNA-29b and miRNA-29c.

6. The method according to claim 1, wherein said antagonist is selected from antisense DNA- and/or RNA-oligonucleotides, antisense 2'-O-methyl oligoribonucleotides, antisense oligonucleotides containing phosphorothiaote linkages, antisense oligonucleotides containing Locked Nucleic Acid bases, morpholino antisense oligonucleotides, PPAR-gamma agonists, antagomirs, and mixtures thereof.

7. The method according to claim 1, wherein said antagonist is administered to the arterial tissue by a drug-eluting stent or by a balloon.

8. The method, according to claim 1, wherein said aortic aneurysm involves a down-regulation of a gene selected from COL1A1, COL1A2, COL1A3, ELN and FBN1.

9. The method, according to claim 1, wherein said miRNA-29 is miRNA-29b.

\* \* \* \* \*

UNITED STATES PATENT AND TRADEMARK OFFICE
CERTIFICATE OF CORRECTION

| | | |
|---|---|---|
| PATENT NO. | : 9,062,307 B2 | Page 1 of 1 |
| APPLICATION NO. | : 13/637924 | |
| DATED | : June 23, 2015 | |
| INVENTOR(S) | : Zeiher et al. | |

It is certified that error appears in the above-identified patent and that said Letters Patent is hereby corrected as shown below:

Title Page, item (54) and in the Specification, Column 1, lines 1-3, Title,
"Antagonists of MIRNA-29 Expression and Their Use in the Prevention and Treatment of Aneurysm" should read
--Antagonists of MIRNA-29 Expression and Their Use in the Prevention and Treatment of Aortic Aneurysms--.

Signed and Sealed this
Second Day of August, 2016

Michelle K. Lee
*Director of the United States Patent and Trademark Office*